US009669104B2

(12) United States Patent
Ganguli et al.

(10) Patent No.: US 9,669,104 B2
(45) Date of Patent: *Jun. 6, 2017

(54) NANOCOMPLEX CONTAINING AMPHIPATHIC PEPTIDE USEFUL FOR EFFICIENT TRANSFECTION OF BIOMOLECULES

(71) Applicant: Council of Scientific and Industrial Research, New Delhi (IN)

(72) Inventors: Munia Ganguli, Delhi (IN); Rajpal, Delhi (IN); Shivangi Shivpuri, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/441,377

(22) PCT Filed: Oct. 31, 2013

(86) PCT No.: PCT/IN2013/000672
§ 371 (c)(1),
(2) Date: May 7, 2015

(87) PCT Pub. No.: WO2014/072997
PCT Pub. Date: May 15, 2014

(65) Prior Publication Data
US 2016/0175455 A1 Jun. 23, 2016

(30) Foreign Application Priority Data
Nov. 7, 2012 (IN) .......................... 3436/DEL/2012

(51) Int. Cl.
*C07K 7/08* (2006.01)
*A61K 48/00* (2006.01)
*C12N 9/16* (2006.01)
*A61K 47/48* (2006.01)
*C12N 15/87* (2006.01)
*A61K 31/7088* (2006.01)

(52) U.S. Cl.
CPC .... *A61K 47/48315* (2013.01); *A61K 31/7088* (2013.01); *A61K 47/48246* (2013.01); *A61K 48/0041* (2013.01); *A61K 48/0091* (2013.01); *C07K 7/08* (2013.01); *C12N 9/16* (2013.01); *C12N 15/87* (2013.01); *C12Y 301/03016* (2013.01)

(58) Field of Classification Search
CPC .......... A61K 31/7088; A61K 47/48315; A61K 47/48323; A61K 48/0041; A61K 48/0091; C07K 7/08; C12N 15/87; C12N 9/16
USPC .......... 428/402; 435/320.1, 455, 91.1, 91.4; 530/322, 326
See application file for complete search history.

(56) References Cited

U.S. PATENT DOCUMENTS 7,569,389 B2 * 8/2009 Feldmann ............ C07K 14/415
                                                    435/419
8,574,861 B2 * 11/2013 Von Der
                        Kammer ............ G01N 33/6896
                                                    435/6.16

FOREIGN PATENT DOCUMENTS

WO    WO-2009/046220    4/2009
WO    WO-2014/072997    5/2014

OTHER PUBLICATIONS

"International Application No. PCT/IN2013/000672, International Preliminary Report on Patentability dated Jan. 28, 2015", (Jan. 28, 2015), 17 pgs.
"International Application No. PCT/IN2013/000672, International Search Report and Written Opinion mailed Apr. 17, 2014", (Apr. 17, 2014), 13 pgs.
Hart, Stephen L., "Multifunctional nanocomplexes for gene transfer and gene therapy", Cell Biology and Toxicology, Feb. 2010, vol. 26, Issue 1, pp. 69-81, (Feb. 3, 2010), 69-81.
Kim, Won Jong, et al., "Cholesteryl Oligoarginine Delivering Vascular Endothelial Growth Factor siRNA Effectively Inhibits Tumor Growth in Colon Adenocarcinoma", Molecular Therapy vol. 14, No. 3, Sep. 2006, 343-350, (Sep. 2006), 343-350.
Lesage, Bart, et al., "Determinants of the nucleolar targeting of protein phosphatase-1", FEBS Letters 579 (2005) 5626-5630; Sep. 29, 2005, (Sep. 29, 2005), 5626-5630.
Mann, Anita, et al., "Linear Short Histidine and Cysteine Modified Arginine Peptides Constitute a Potential Class of DNA Delivery Agents", Molecular Pharmaceutics (Impact Factor: 4.79). Jan. 2014; 11(3), 683-696, (Mar. 3, 2014), 683-696.
Martin, Molly E., et al., "Peptide-guided Gene Delivery", The AAPS Journal 2007; 9 (1) Article 3 (http://www.aapsj.org), (Feb. 9, 2007), 12 pgs.
Naik, Rangeetha J., et al., "Different roles of cell surface and exogenous glycosaminoglycans in controlling gene delivery by arginine-rich peptides with varied distribution of arginines", Biochimica et Biophysica Acta 1828 (2013) 1484-1493, (Feb. 26, 2013), 1484-1493.
Sharma, Rajpal, "Insight into the Role of Physicochemical Parameters in a Novel Series of Amphipathic Peptides for Efficient DNA Delivery", Molecular Pharmaceutics (Impact Factor: 4.79). Jun. 2013; 10(7), 2588-2600, (Jul. 1, 2013), 2588-2600.

(Continued)

*Primary Examiner* — Julie Ha
(74) *Attorney, Agent, or Firm* — Schwegman Lundberg & Woessner, P.A.

(57) ABSTRACT

A nanocomplex useful for efficient transfection and delivery of biomolecules comprising amphipathic peptide sequence is provided. For example, amphipathic peptides for the delivery of biomolecules to eukaryotic cells are provided. These peptide based vectors can form stable nanocomplex with biomolecules mainly with nucleic acids and can deliver it efficiently to cells. The complexation can be done non-covalently with small as well as large biomolecules.

16 Claims, 8 Drawing Sheets

(56) References Cited

OTHER PUBLICATIONS

Sharma, Rajpal, "Structural rearrangements and chemical modifications in known cell penetrating peptide strongly enhance DNA delivery efficiency", Journal of Controlled Release, vol. 157, Issue 2, Jan. 30, 2012, pp. 260-271, (Jan. 30, 2012), 260-271.

Bartz, Rene, et al., "Effective siRNA delivery and target mRNA degradation using an amphipathic peptide to facilitate pH-dependent endosomal escape", *Biochem. J.*, 435, (2011), 475-487.

Edelstein, Michael L., et al., "Gene therapy clinical trials worldwide to 2007—an update", *J. Gene Med.*, 9, (2007), 833-842.

Elmquist, Anna, et al., "VE-Cadherin-Derived Cell-Penetrating Peptide, pVEC, with Carrier Functions", *Experimental Cell Research*, 269, (2001), 237-244.

Fabre, John' W., et al., "Synthetic Peptides As Non-Viral DNA Vectors", *Current Gene Therapy*, 6, (2006), 459-480.

Fernández-Carneado, Jimena, et al., "Amphipathic Peptides and Drug Delivery", *Biopolymers (Peptide Science)*, vol. 76, (2004), 196-203.

Fischer, Dagmar, et al., "In vitro cytotoxicity testing of polycations: influence of polymer structure on cell viability hemolysis", *Biomaterials*, 24, (2003), 1121-1131.

Fominaya, Jesús, et al., "An optimized amphiphilic cationic peptide as an efficient non-viral gene delivery vector", *The Journal of Gene Medicine*, 2, (2000), 455-464.

Gautier, Romain, et al., "HELIQUEST: a web server to screen sequences with specific α-helical properties", *Bioinformatics*, 24(18), (2008), 2101-2102.

Kuriyama, Shinichi, et al., "Peptide vector for gene delivery with high affinity for phosphatidylserine", *Journal of Peptide Science*, 12, (2006), 626-632.

Liu, Dexi, et al., "Cationic Transfection Lipids", *Current Medicinal Chemistry*, 10, (2003), 1307-1315.

Mintzer, Meredith A., et al., "Nonviral Vectors for Gene Delivery", *Chem. Rev.*, 109(2), (2009), 259-302.

Niidome, T., et al., "Gene Therapy Progress and Prospects: Nonviral vectors", *Gene Therapy*, 9, (2002), 1647-1652.

Niidome, T., et al., "Influence of lipophilic groups in cationic α-helical peptides on their abilities to bind with DNA and deliver genes into cells", *J Pept Res.*, 54(4), (1999), 361-367.

Niidome, Takuro, et al., "Binding of cationic α-helical peptides to plasmid DNA and their gene transfer abilities into cells", *J. Biol Chem.*, 272(24), (1997), 15307-15312.

Niidome, Takuro, et al., "Gene transfer into hepatoma cells mediated by galactose-modified α-helical peptides", *Biomaterials*, 21, (2000), 1811-1819.

Oehlke, Johannes, et al., "Enhancement of intracellular concentration and biological activity of PNA after conjugation with a cell-penetrating synthetic model peptide", *Eur. J. Biochem.*, 271, (2004), 3043-3049.

Remaut, Katrien, et al., "Nucleic acid delivery: Where material sciences and bio-sciences meet", *Materials Science and Engineering*, R 58, (2007), 117-161.

Won, Young-Wook, et al., "Poly(oligo-D-arginine) With Internal Disulfide Linkages as a Cytoplasm-sensitive Carrier for siRNA Delivery", *Molecular Therapy*, 19(2), (Feb. 2011), 372-380.

Won, Young-Wook, et al., "Reducible Poyl(oligo-D-argnine) for Enhanced Gene Expression in Mouse Lung by Intratracheal Injection", *Molecular Therapy*, 18(4), (Apr. 2010), 734-742.

Wyman, Tara B., "Design, Synthesis, and Characterization of a Cationic Peptide That Binds to Nuckeic Acids and Permeabilizes Bilayers", *Biochemistry*, 36, (1997), 3008-3017.

* cited by examiner

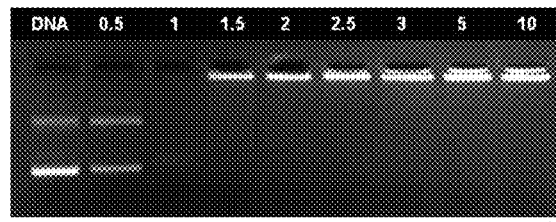
Figure 1A
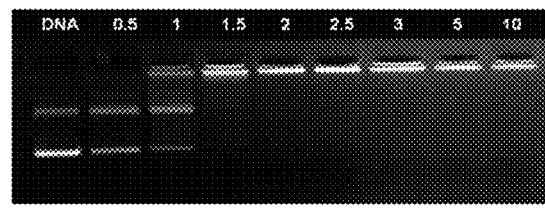
Figure 1B
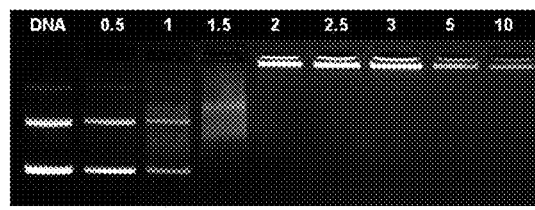
Figure 1C
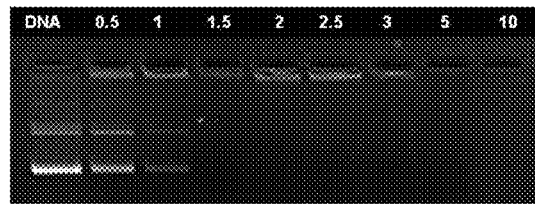
Figure 1D
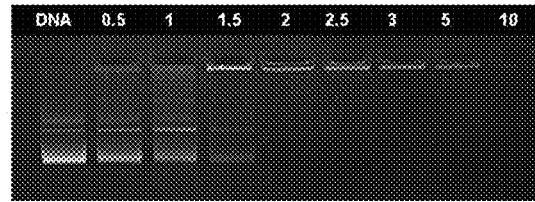
Figure 1E
FIGURE 1

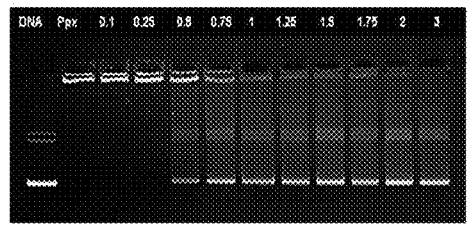
Figure-2A
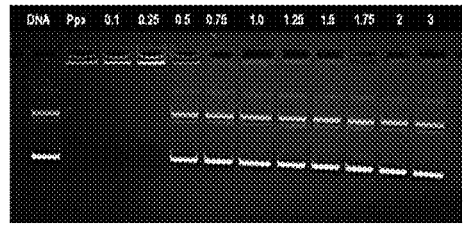
Figure-2B
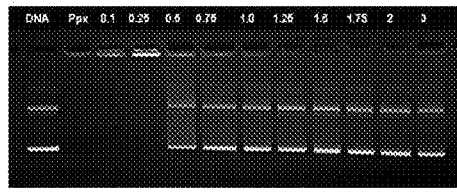
Figure-2C
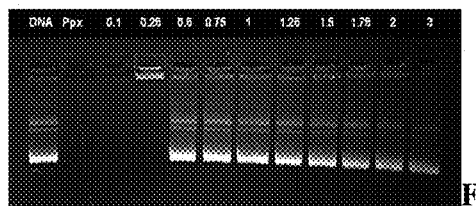
Figure-2D
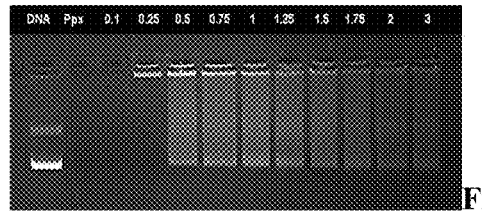
Figure-2E
FIGURE 2

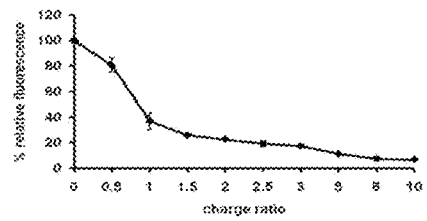
Figure- 3A
Figure- 3B
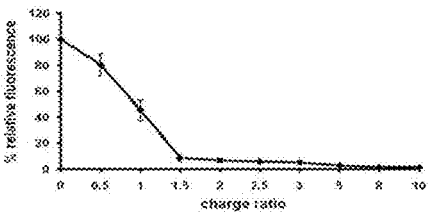
Figure- 3C
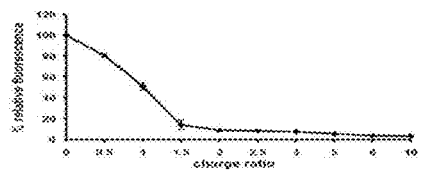
Figure- 3D
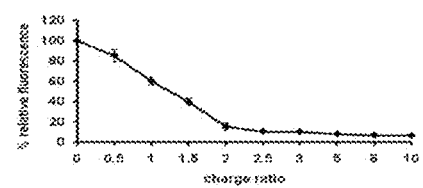
Figure- 3E
FIGURE 3

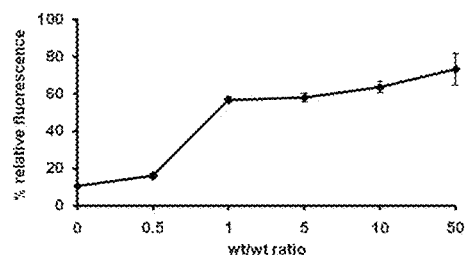
Figure-4
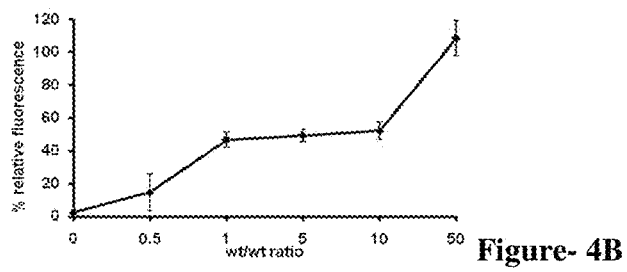
Figure- 4B
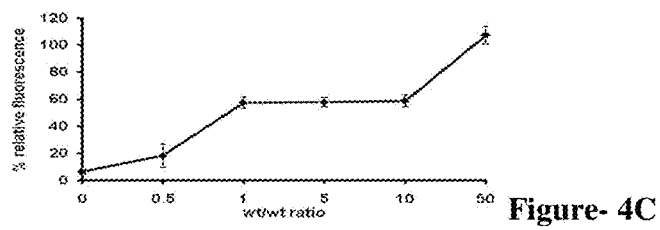
Figure- 4C
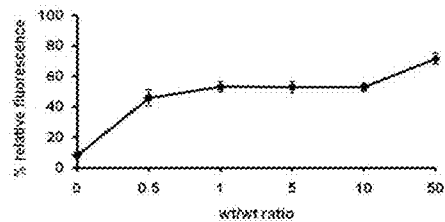
Figure- 4D
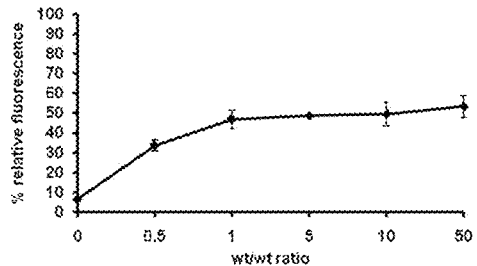
Figure- 4E
FIGURE- 4

FIGURE 7A: MCF7 cells          FIGURE 7B: A549 cells

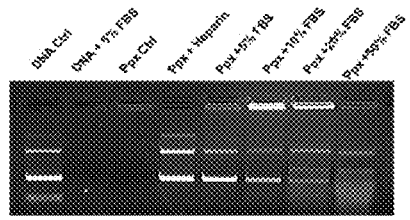
Figure 8A
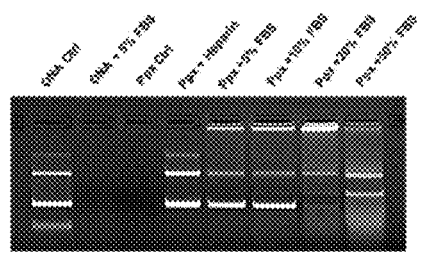
Figure 8B
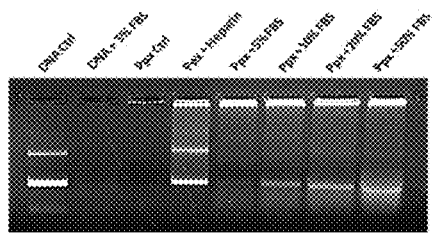
Figure 8C
Figure 8
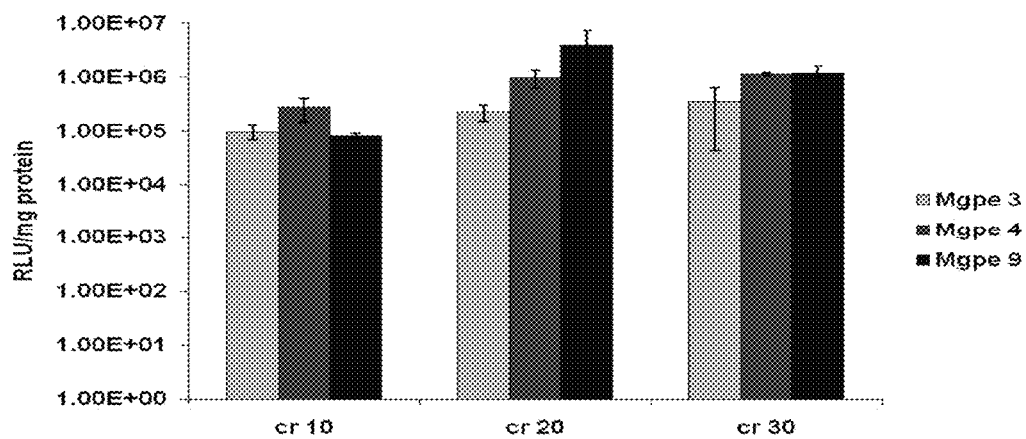
FIGURE 9

SEQUENCE LISTING

<160> NUMBER OF SEQ ID NOS: 6

<210> SEQ ID NO 1
<211> LENGTH: 755
<212> TYPE: PRT
<213> ORGANISM: Homo sapiens

<400> SEQUENCE: 1

```
Met Ala Gly Cys Ile Pro Glu Glu Lys Thr Tyr Arg Arg Phe Leu Glu
1               5                   10                  15

Leu Phe Leu Gly Glu Phe Arg Gly Pro Cys Gly Gly Gly Glu Pro Glu
            20                  25                  30

Pro Glu Pro Glu Pro Glu Pro Glu Pro Glu Ser Glu Pro Glu
        35                  40                  45

Pro Glu Pro Glu Leu Val Glu Ala Glu Ala Glu Ala Ser Val Glu
    50                  55                  60

Glu Pro Gly Glu Glu Ala Ala Thr Val Ala Ala Thr Glu Glu Gly Asp
65                  70                  75                  80

Gln Glu Gln Asp Pro Glu Pro Glu Glu Ala Val Glu Gly Glu
                85                  90                  95

Glu Glu Glu Glu Gly Ala Ala Thr Ala Ala Ala Pro Gly His Ser
                100                 105                 110

Ala Val Pro Pro Pro Pro Gln Leu Pro Pro Leu Pro Pro Leu Pro
            115                 120                 125

Arg Pro Leu Ser Glu Arg Ile Thr Arg Glu Glu Val Glu Gly Glu Ser
130                 135                 140

Leu Asp Leu Cys Leu Gln Gln Leu Tyr Lys Tyr Asn Cys Pro Ser Phe
145                 150                 155                 160

Leu Ala Ala Ala Leu Ala Arg Ala Thr Ser Asp Glu Val Leu Gln Ser
                165                 170                 175

Asp Leu Ser Ala His Tyr Ile Pro Lys Glu Thr Asp Gly Thr Glu Gly
            180                 185                 190

Thr Val Glu Ile Glu Thr Val Lys Leu Ala Arg Ser Val Phe Ser Lys
        195                 200                 205

Leu His Glu Ile Cys Cys Ser Trp Val Lys Asp Phe Pro Leu Arg Arg
210                 215                 220

Arg Pro Gln Leu Tyr Tyr Glu Thr Ser Ile His Ala Ile Lys Asn Met
225                 230                 235                 240

Arg Arg Lys Met Glu Asp Lys His Val Cys Ile Pro Asp Phe Asn Met
                245                 250                 255

Leu Phe Asn Leu Glu Asp Gln Glu Glu Gln Ala Tyr Phe Ala Val Phe
            260                 265                 270

Asp Gly His Gly Gly Val Asp Ala Ala Ile Tyr Ala Ser Ile His Leu
        275                 280                 285

His Val Asn Leu Val Arg Gln Glu Met Phe Pro His Asp Pro Ala Glu
290                 295                 300

Ala Leu Cys Arg Ala Phe Arg Val Thr Asp Glu Arg Phe Val Gln Lys
305                 310                 315                 320

Ala Ala Arg Glu Ser Leu Arg Cys Gly Thr Thr Gly Val Val Thr Phe
                325                 330                 335

Ile Arg Gly Asn Met Leu His Val Ala Trp Val Gly Asp Ser Gln Val
            340                 345                 350

Met Leu Val Arg Lys Gly Gln Ala Val Glu Leu Met Lys Pro His Lys
        355                 360                 365

Pro Asp Arg Glu Asp Glu Lys Gln Arg Ile Glu Ala Leu Gly Gly Cys
370                 375                 380

Val Val Trp Phe Gly Ala Trp Arg Val Asn Gly Ser Leu Ser Val Ser
385                 390                 395                 400
```

```
Arg Ala Ile Gly Asp Ala Glu His Lys Pro Tyr Ile Cys Gly Asp Ala
            405                 410                 415

Asp Ser Ala Ser Thr Val Leu Asp Gly Thr Glu Asp Tyr Leu Ile Leu
            420                 425                 430

Ala Cys Asp Gly Phe Tyr Asp Thr Val Asn Pro Asp Glu Ala Val Lys
            435                 440                 445

Val Val Ser Asp His Leu Lys Glu Asn Asn Gly Asp Ser Ser Met Val
            450                 455                 460

Ala His Lys Leu Val Ala Ser Ala Arg Asp Ala Gly Ser Ser Asp Asn
465                 470                 475                 480

Ile Thr Val Ile Val Phe Leu Arg Asp Met Asn Lys Ala Val Asn
            485                 490                 495

Val Ser Glu Glu Ser Asp Trp Thr Glu Asn Ser Phe Gln Gly Gly Gln
            500                 505                 510

Glu Asp Gly Gly Asp Lys Glu Asn His Gly Glu Cys Lys Arg Pro
            515                 520                 525

Trp Pro Gln His Gln Cys Ser Ala Pro Ala Asp Leu Gly Tyr Asp Gly
            530                 535                 540

Arg Val Asp Ser Phe Thr Asp Arg Thr Ser Leu Ser Pro Gly Ser Gln
545                 550                 555                 560

Ile Asn Val Leu Glu Asp Pro Gly Tyr Leu Asp Leu Thr Gln Ile Glu
            565                 570                 575

Ala Ser Lys Pro His Ser Ala Gln Phe Leu Leu Pro Val Glu Met Phe
            580                 585                 590

Gly Pro Gly Ala Pro Lys Lys Ala Asn Leu Ile Asn Glu Leu Met Met
            595                 600                 605

Glu Lys Lys Ser Val Gln Ser Ser Leu Pro Glu Trp Ser Gly Ala Gly
            610                 615                 620

Glu Phe Pro Thr Ala Phe Asn Leu Gly Ser Thr Gly Glu Gln Ile Tyr
625                 630                 635                 640

Arg Met Gln Ser Leu Ser Pro Val Cys Ser Gly Leu Glu Asn Glu Gln
            645                 650                 655

Phe Lys Ser Pro Gly Asn Arg Val Ser Arg Leu Ser His Leu Arg His
            660                 665                 670

His Tyr Ser Lys Lys Trp His Arg Phe Arg Phe Asn Pro Lys Phe Tyr
            675                 680                 685

Ser Phe Leu Ser Ala Gln Glu Pro Ser His Lys Ile Gly Thr Ser Leu
            690                 695                 700

Ser Ser Leu Thr Gly Ser Gly Lys Arg Asn Arg Ile Arg Ser Ser Leu
705                 710                 715                 720

Pro Trp Arg Gln Asn Ser Trp Lys Gly Tyr Ser Glu Asn Met Arg Lys
            725                 730                 735

Leu Arg Lys Thr His Asp Ile Pro Cys Pro Asp Leu Pro Trp Ser Tyr
            740                 745                 750

Lys Ile Glu
        755

<210> SEQ ID NO 2
<211> LENGTH: 18
<212> TYPE: PRT
<213> ORGANISM: Homo sapiens

<400> SEQUENCE: 2

Ser Arg Leu Ser His Leu Arg His His Tyr Ser Lys Lys Trp His Arg
```

-continued

```
                1               5              10              15

Phe Arg

<210> SEQ ID NO 3
<211> LENGTH: 18
<212> TYPE: PRT
<213> ORGANISM: Artificial Sequence
<220> FEATURE:
<223> OTHER INFORMATION: A synthetic polypeptide

<400> SEQUENCE: 3

Arg Arg Leu Arg His Leu Arg His His Tyr Arg Arg Arg Trp His Arg
1               5                   10                  15

Phe Arg

<210> SEQ ID NO 4
<211> LENGTH: 18
<212> TYPE: PRT
<213> ORGANISM: Artificial Sequence
<220> FEATURE:
<223> OTHER INFORMATION: A synthetic polypeptide

<400> SEQUENCE: 4

Leu Leu Tyr Trp Phe Arg Arg Arg His Arg His His Arg Arg Arg His
1               5                   10                  15

Arg Arg

<210> SEQ ID NO 5
<211> LENGTH: 20
<212> TYPE: PRT
<213> ORGANISM: Artificial Sequence
<220> FEATURE:
<223> OTHER INFORMATION: A synthetic polypeptide

<400> SEQUENCE: 5

Cys Arg Arg Leu Arg His Leu Arg His His Tyr Arg Arg Arg Trp His
1               5                   10                  15

Arg Phe Arg Cys
            20

<210> SEQ ID NO 6
<211> LENGTH: 20
<212> TYPE: PRT
<213> ORGANISM: Artificial Sequence
<220> FEATURE:
<223> OTHER INFORMATION: A synthetic polypeptide

<400> SEQUENCE: 6

Cys Leu Leu Tyr Trp Phe Arg Arg Arg His Arg His His Arg Arg Arg
1               5                   10                  15

His Arg Arg Cys
            20
```

NANOCOMPLEX CONTAINING AMPHIPATHIC PEPTIDE USEFUL FOR EFFICIENT TRANSFECTION OF BIOMOLECULES

PRIORITY CLAIM TO RELATED APPLICATIONS

This application is a U.S. national stage application filed under 35 U.S.C. §371 from International Application Serial No. PCT/IN2013/000672, which was filed 31 Oct. 2013, and published as WO 2014/072997 on 15 May 2014, and which claims priority to India Application No. 3436/DEL/2012, filed 7 Nov. 2012, which applications and publication are incorporated by reference as if reproduced herein and made a part hereof in their entirety, and the benefit of priority of each of which is claimed herein.

FIELD OF THE INVENTION

The present invention provides a nanocomplex useful for efficient transfection and delivery of biomolecules comprising amphipathic peptide sequence Mgpe-3 (SEQ ID NO:3), Mgpe-4 (SEQ ID NO:4), Mgpe-9 (SEQ ID NO:5) and Mgpe-10 (SEQ ID NO:6) generated by modifying the primary sequence of the Mgpe-1 (SEQ ID NO:2). The peptide sequence Mgpe-1 is derived from HUMAN Protein phosphatase 1E (SEQ ID NO:1).

BACKGROUND OF THE INVENTION

Development of nano carriers to introduce nucleic acids into cells has been of considerable interest in biomedical research because of the potential of exogenously delivered therapeutic nucleic acids to cure several genetic as well as complex disorders [Edelstein et al., 2007]. Viral vectors are most explored in this context but have been found in many cases to be unsafe for clinical use because of associated immune response and random integration in host genome. A variety of materials (cationic lipids and polymers) have been used to facilitate the delivery of nucleic acids into the cells [Meredith et al (2009), Niidome et al (2002)]. But most of these materials have limitations like low transfection efficiency, high cytotoxicity and complicated synthesis procedure which leads to limited product yield [Mintzer et. al., 2009; Remaut et. al., 2007]. For example, although liposomes are attractive materials for drug delivery applications, application of liposomes for DNA delivery is plagued by problems like cytotoxicity, serum instability, changes in size, surface charge and lipid composition of the lipid-DNA complex during delivery and so on (Liu et al., 2003). Cationic polymers have been used as a substitute of lipid based vectors but most polymers also exhibit some major disadvantages, e.g. complicated synthetic procedure, lack of control during synthesis which ultimately reflects in non-uniform physico-chemical properties, low biodegradability and high toxicity. Besides there are difficulties of selectively modifying the polymer with ligands for targeted delivery. One of the cationic polymers extensively used for gene delivery, poly (ethyleneimine) (PEI), suffers due to its non-biodegradable nature leading to cellular toxicity (Fischer et al., 2003).

Peptides constitute a promising class of non-viral vectors as they are easy to synthesize, amenable to modifications for the attachment of different functional moieties, relatively small in size and are the most biocompatible class of delivery vectors [Fabre et al 2006]. Peptides used for nucleic acid delivery can be categorized into two classes: cationic peptides and amphipathic peptides. Amphipathic peptides are made of both hydrophobic and hydrophilic amino acids [Fernandez-Carneado, 2004]. The basic framework of the cell membrane is made up of amphipathic lipids; hence amphipathic peptides can interact with the membrane in a more efficient manner and allow cargo uptake [Fomiyana et al., 2000; Kuriyama et al., 2006; Bartz et al., 2011; Oehlke et al., 2004; Niidome et al., 2000]. Therefore naturally occurring as well as synthetically designed amphipathic peptides are of great interest as delivery vectors [Elmquist et al (2001) and Wyman et al (1997)]. Most amphipathic peptides possess the ability to translocate across the cell membrane. Efficient cellular uptake and endosomal escape properties of these peptides are the main reasons for their development as carriers of therapeutic cargo molecules. However, most of these peptides are not effective carriers of large cargoes like plasmid DNA and it is important to optimally design the peptide to improve the delivery efficiency [Rajpal et al (2012)]. The hydrophobicity and positive charge are two most important parameters of the peptide which need to be optimized for designing an amphipathic peptide which can deliver plasmid DNA with high efficiency through formation of a nanocomplex. The hydrophobic amino acids of the peptide interact with membrane and help in cellular uptake of the nanocomplex and positive charged amino acids of the peptide condense DNA to form these nano complexes. A minimum amount of each of these two types of amino acids is required; however the proportion of these two residues should be optimized because high hydrophobicity as well as positive charge (arginine) can cause cellular toxicity, and tight packaging of DNA reduces the accessibility of DNA to transcription machinery [Mann et al (2011)]. On the other hand, less number of positive charges and low hydrophobicity can lead to premature degradation of the DNA and poor cellular uptake [Niidome et al (1997) and Niidome et al (1999)].

In the present invention, nanocomplex has been prepared containing Mgpe peptides. The peptide Mgpe-1 (SEQ ID NO:2) (derived from Human Protein phosphatase 1E (SEQ ID NO:1) is a novel amphipathic peptide for biomolecule delivery and we further altered its physicochemical parameters and generated five novel peptides to achieve efficient delivery of plasmid DNA and small nucleic acid. The primary sequence of Mgpe-1 peptide is SRLSHLRHHYSK-KWHRFR (Mgpe1) (SEQ ID NO:2). In a modification of Mgpe-1 (SEQ ID NO:2) total charges have been increased from 6 to 9 and Mgpe-3 has been generated (RRLRHLRH-HYRRRWHRFR) (SEQ ID NO:3). Further, a peptide Mgpe-4 (LLYWFRRRHRHHRRRHRR) (SEQ ID NO:4) has been generated by altering the amphipathicity of Mgpe-3 from secondary to primary by altering the position of amino acids. These two peptides (Mgpe-3 and Mgpe-4) were further modified by addition of two cysteine residues at both ends. These two primary sequences are CRRLRHLRHHY-RRRWHRFRC and CLLYWFRRRHRHHRRRHRRC (Mgpe 9 and Mgpe 10, SEQ ID Nos. 5 and 6, respectively). All modified Mgpe peptides were generated in such a way as to optimize the total content of hydrophobicity, charges, amphipathicity and amino acid composition and were developed by modifying the primary sequence of the Mgpe-1 peptide (SEQ ID NO:2) sequentially. All the peptides formed nanocomplexes with plasmid DNA with particle sizes 50-110 nm and exhibited high transfection efficiency in multiple cell lines with negligible or very low toxicity.

OBJECTIVE OF THE INVENTION

The main object of the present invention is to provide a nanocomplex useful for efficient transfection of biomolecules using Mgpe peptides. Another object of the present invention is to develop a peptide having inherent property to non-covalently interact with large DNA and make nanocomplexes.

Yet another object of the present invention is to develop a delivery system that can deliver plasmid DNA into cells with efficiency equivalent to or better than known commercial transfection agents.

Still another object of the present invention is to provide a DNA delivery system that transfects a variety of cell lines efficiently with low toxicity.

Yet another object of the present invention is to develop a DNA delivery system which has inherent property to efficiently overcome endosomal barrier while delivering the cargo.

Yet another object of the present invention is to provide a nanocomplex which will protect the cargo from serum degradation.

Still another object of the present invention is to provide an amphipathic peptide-based nanocomplex system that can deliver siRNA and other small nucleic acids into cells.

SUMMARY OF THE INVENTION

Accordingly, the present invention provides a nanocomplex useful for efficient transfection of biomolecules comprising peptides Mgpe-3, Mgpe-4, Mgpe-9 and Mgpe-10 generated by modifying the primary sequence of the Mgpe-1 (SEQ ID NO:2). Mgpe-1 (SEQ ID NO:2) is derived from HUMAN Protein phosphatase 1E (SEQ ID NO:1). The present invention provides an eighteen amino acid long peptide containing six positive charges, three histidines and serines and one tryptophan with secondary amphipathicity (SRLSHLRHHYSKKWHRFR) which has been modified and a peptide Mgpe-3 (SEQ ID NO:3) has been generated where the total charge of the peptide is increased to 9 replacing three serines with arginines (RRLRHLRHHYR-RRWHRFR; SEQ ID NO:3).

In an embodiment of the present invention, there is provided a nanocomplex useful for efficient transfection characterised in containing sequences selected from the group consisting of SEQ ID NO:3, SEQ ID NO:4, SEQ ID NO:5 and SEQ ID NO:6.

In an embodiment of the present invention, there is provided a nanocomplex wherein the sequence is an amphipathic Mgpe peptide.

In an embodiment of the present invention, there is provided a nanocomplex wherein the peptide is operably linked to a biomolecule.

In an embodiment of the present invention, there is provided a nanocomplex wherein the biomolecule is selected from the group comprising of a DNA, plasmid DNA, RNA, an antisense nucleotide, an aptamer, a protein, a glycoprotein, a polypeptide, a carbohydrate or a mixture or adduct of any two or more of these.

In an embodiment of the present invention a nanocomplex gives maximal transfection efficiency of 7-9 orders in RLU/mg protein with minimal cytotoxicity.

In an embodiment of the present invention a nanocomplex has a size in the range of 50-110 nm.

In yet another embodiment of the present invention, there is provided a method of preparing the nanocomplex comprising steps:
a) providing Mgpe peptide;
b) providing biomolecule;
c) diluting the peptide 10-100 µl obtained in step (a) and DNA 20-50 ng/µl obtained in step (b) in water such that peptide-DNA charge ratio is 0.5-50;
d) adding DNA solution obtained in step (b) drop-wise to an equal volume of the peptide dilution while vortexing;
e) incubating solution obtained in step (d) for 30 min to 1 h at room temperature to obtain the nanocomplex.

In yet another embodiment of the present invention, there is provided a nanocomplex wherein it carries biomolecules in the range of 20 bp to 7 kbp size.

In yet another embodiment of the present invention, there is provided a kit useful for delivering biomolecules into a cell, said kit comprising of Mgpe peptide and an instruction manual.

In a further embodiment of the present invention, there is provided use of nanocomplex, for efficient delivery of biomolecules into the cells with minimal toxicity.

In a further embodiment of the present invention, there is provided use of nanocomplex as a peptide based carrier system.

In a further embodiment of the present invention, there is provided use of nanocomplex for protection of biomolecules in presence of serum and efficient transfection in eukaryotic cells in serum containing medium.

In a further embodiment of the present invention, there is provided use of the nanocomplex, for efficiently transfection of biomolecules into an eukaryotic cell.

In yet another embodiment of the present invention, there is provided a composition, comprising: (a) nanocomplex that comprise (i) an amphipathic peptide that comprises less than 30 amino acids and (ii) a lipid and (b) at least one cell specific targeting ligand or immunogenic species or a drug associated with said nanocomplexes.

In yet another embodiment of the present invention, there is provided the composition, wherein the amphipathic peptide comprises an amino acid sequence selected from the group consisting of SEQ ID NO:3, SEQ ID NO:4, SEQ ID NO:5 and SEQ ID NO: 6.

In yet another embodiment of the present invention, there is provided a composition, wherein the lipid is a phospholipid and cholesterol.

In yet another embodiment of the present invention, there is provided a method of forming cell specific targeting composition or immunogenic composition or drug delivery composition, comprising synthesizing or modifying an immunogenic species or cell specific targeting ligand or a drug in the presence of nanocomplexes that comprise (i) an amphipathic peptide that comprises less than 30 amino acids and (ii) a lipid, wherein said synthesized or modified cell specific targeting ligand or immunogenic species or a drug becomes associated with said nanocomplexes as a result of said synthesis or modification step.

In an embodiment of the present invention, Mgpe-3 has been further modified to Mgpe-4 (LLYW-FRRRHRHHRRRHRR) (SEQ ID NO:4) where a secondary amphipathic peptide (Mgpe-3) is changed to primary amphipathic peptide (Mgpe-4) by rearrangement of the amino acids.

In another embodiment of the present invention, two cysteines were incorporated on the two ends of the peptides Mgpe-3 and Mgpe-4 respectively to generate two peptides Mgpe-9 and Mgpe-10 (SEQ ID Nos. 5 and 6).

In still another embodiment of the present invention, peptide-DNA nanocomplexes were prepared at different charge ratios ranging from 0.5 to 50 expressed as peptide nitrogen per nucleic acid phosphate (N/P) or as Z (+/−) by mixing peptides and plasmid DNA or RNA followed by vortexing and allowing the complexes to stabilize.

In yet another embodiment of the present invention, all five invented peptides were able to condense large plasmid DNA non-covalently and efficiently to form nanocomplexes. All the peptides retarded the DNA on agarose gel at charge ratio 1.5 to 2. Similarly 80-90% fluorescence decreases have been observed in ethidium bromide (EtBr) assay at charge ratio 1.5 to 2 in all the cases.

In still another embodiment of the present invention, all five invented peptides were able to make monodisperse nanocomplexes with sizes ranging from 50 nm to 110 nm with DNA (size ranging from 3-7 kb).

In yet another embodiment of the present invention, all the nanocomplexes showed an ability to release the DNA when encountered with the anionic challenge (using anionic agent heparin; heparin:peptide ratio of 0.25 to 1) which is primary requirement for efficient delivery of bioactive molecules.

In still another embodiment of the present invention, Mgpe-9 and Mgpe-10 have two cysteines and these peptides further have possibilities to be used as reducible polycations where the peptide has been polymerized before making a nanocomplex with the DNA or the nanocomplex is oxidized after preparation to further increase the transfection efficiency.

In yet another embodiment of the present invention, nanocomplexes from all the five peptides show good transfection efficiency of plasmid DNA in CHO-K1 cells while non-covalently complexed. Peptide Mgpe-9 shows maximum transfection efficiency which is more than $10^8$ RLU/mg protein at charge ratio 5.

In still another embodiment of the present invention, these nanocomplexes show higher or equal transfection efficiency in comparison with liposomal and PEI based commercial transfection agents like Cellfectin, Superfect and Lipofectamine 2000.

In yet another embodiment of the present invention, nanocomplex containing peptide Mgpe-3 shows higher or equal transfection efficiency to the commercially available agent Cellfectin and Superfect in CHO-K1 cells at charge ratio 10.

In still another embodiment of the present invention, nanocomplex containing peptide Mgpe-4 shows higher or equal transfection efficiency to the commercially available agent Cellfectin and Superfect in CHO-K1 cells at charge ratio 5.

In yet another embodiment to the present invention, nanocomplex containing peptide Mgpe-9 shows higher or equal transfection efficiency to the commercially available agent Cellfectin, Superfect and Lipofectamine 2000 in CHO-K1 cells at charge ratio 5.

In still another embodiment to the present invention, presence of chloroquine shows only slight increase in transfection efficiency indicating these peptides present in nanocomplex have inherent property to come out of the endosomal barrier.

In yet another embodiment of present invention, nanocomplexes containing these peptides show promising transfection efficiency in many cell lines from different origin like MCF-7, A549 and CHO-K1 cells. Nanocomplex containing Mgpe-9 shows highest transfection efficiency at charge ratio 5 which is more than $10^8$ RLU/mg protein in CHO-K1, more than $10^8$ RLU/mg protein in MCF-7, more than $10^6$ RLU/mg protein in A549 cell lines.

In still another embodiment of present invention, these nanocomplexes show serum stability at different serum concentrations.

In yet another embodiment of the present invention, nanocomplexes containing these peptides show good transfection efficiency in presence of 10% serum in CHO-K1 cells at different charge ratio like 10, 20 and 30. At charge ratio of 20 nanocomplex containing Mgpe-9 shows highest transfection efficiency in presence of serum which is up to $10^7$ RLU/mg protein.

In still another embodiment of the present invention, nanocomplexes containing these peptides show none or very less cytotoxicity in CHO-K1 cells which is prerequisite for a better transfection reagent.

In yet another embodiment of the present invention, nanocomplxes containing these peptides show 100-125% less toxicity when compared to Lipofectamine 2000 whereas comparable to Superfect and Cellfectin in CHO-K1 cells.

In still another embodiment of the present invention, nanocomplexes containing peptide Mgpe-9 and Mgpe-10 have been found to show small RNA delivery using Siglo which was non-covalently complexed to the peptide at a charge ratio of 5.

BRIEF DESCRIPTION OF THE FIGURES

FIG. 1 shows the electrophoretic mobility of the nanocomplexes at different charge ratios. Lane 1-Ctrl (only plasmid DNA), Lane 2-9 are the nanocomplexesformed at different charge ratios (0.5-10). FIG. 1A for Mgpe-1 (SEQ ID NO:2), FIG. 1B for Mgpe-3, FIG. 1C for Mgpe-4, FIG. 1D for Mgpe-9 and FIG. 1E for Mgpe-10.

FIG. 2 shows DNA release from the nanocomplex of DNA and peptides at different Wt/Wt ratios of heparin: petide. DNA release assay showing relative stability of nanocomplexes formed with peptides at charge ratio 10.0 against different concentrations (weight/weight ratio of heparin/peptide) of anionic agent. Lane 1-Ctrl (only plasmid DNA), Lane 2-12 are different weight/weight ratios of heparin/peptide (0.0-3.0). FIG. 2A for Mgpe-1 (SEQ ID NO:2), FIG. 2B for Mgpe-3, FIG. 2C for Mgpe-4, FIG. 2D for Mgpe-9 and FIG. 2E for Mgpe-10.

FIG. 3 shows DNA condensation efficiency using Ethidium bromide (EtBr) intercalation assay. The fluorescence of EtBr is inhibited as it excludes from DNA upon increasing concentration of peptides or charge ratio Z (+/−). The fluorescence of free uncomplexed DNA was set as maximum i.e. 100%. Values are plotted as percentage of maximum±S.D. FIG. 3A for Mgpe-1 (SEQ ID NO:2), FIG. 3B for Mgpe-3, FIG. 3C for Mgpe-4, FIG. 3D for Mgpe-9 and FIG. 3E for Mgpe-10.

FIG. 4 shows DNA release efficiency using Ethidium bromide (EtBr) intercalation assay. Relative stability of nanocomplexes at charge ratio 10.0 against different concentrations (weight/weight ratio of heparin/peptide) of anionic agent is shown. Amount of DNA released was measured by increase in the fluorescence because of intercalation of EtBr. Fluorescence of free plasmid DNA complexed to EtBr was taken as 100%. Values are plotted as percentage of maximum±S.D. FIG. 4A for Mgpe-1 (SEQ ID NO:2), FIG. 4B for Mgpe-3, FIG. 4C for Mgpe-4, FIG. 4D for Mgpe-9 and FIG. 4E for Mgpe-10.

FIG. 8 shows serum stability of the DNA complexed with peptides at different concentration of serum. Serum stability assay showing relative stability of nanocomplexes formed with peptides at charge ratio 10.0 in presence of serum. Lane 1-Ctrl (only plasmid DNA), Lane 2-plasmid DNA with 5% serum, Lane 3-nanocomplex only, Lane 4-nanocomplex with heparin, Lane 5-8 nanocomplex with different concentration of serum. FIG. 8A for Mgpe-3, FIG. 8B for Mgpe-4 and FIG. 8C for Mgpe-9. (ppx=nanocomplex)

FIG. 9 shows transfection efficiency; in vitro transfection of the luciferase gene into CHO-K1 in presence of 10% serum. Transfections have been done at charge ratio 10, 20 and 30 for Mgpe-3, Mgpe-4 and Mgpe-9. Cells were incubated with the nanocomplexes for 5 h and luciferase activity was measured after 24 h. (cr=charge ratio)

DETAILED DESCRIPTION OF THE INVENTION

Figure 5:
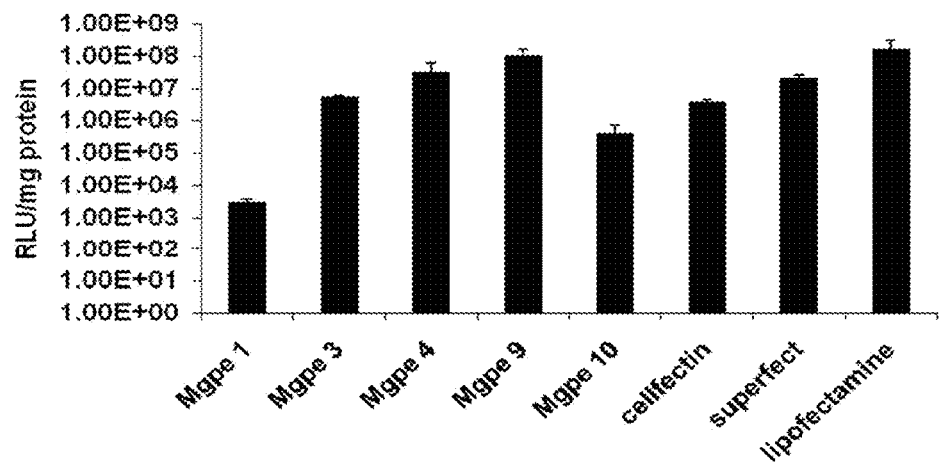
FIG. 5 shows in vitro transfection of the luciferase gene into CHO-K1 cells using the different nanocomplexes containing different Mgpe peptides in comparison with different commercially available transfection reagents. Transfections have been done at charge ration 10 for Mgpe-1 (SEQ ID NO:2) and Mgpe-3 and at charge ratio 5 for Mgpe-4, Mgpe-9 and Mgpe 10. Cells were incubated with the nanocomplexes for 5 h and luciferase activity was measured after 24 h.

Delivering therapeutic biomolecules into the cell has the potential to provide much help in clinics in the treatment of genetic as well as acquired diseases and is also important as a research tool. However, since these foreign therapeutic molecules cannot enter cells on their own and most of their known carrier molecules suffer from several limitations as listed above, there is an urgent need for design and synthesis of novel carrier molecules. Peptides can serve as an efficient delivery vectors as they are easy to synthesise, chemically modified for tissue specific delivery, biocompatible and are safer as compared to their lipid and polymer counterparts. However, many of the known peptide systems suffer from low transfection efficiency. Therefore there is a need to design peptide-based transfection agents which have high transfection efficiency and low cytotoxicity.

A nucleic acid delivery peptide should have nucleic acid binding property and also simultaneously possess the property of membrane interaction. For this purpose, we considered to design a helical amphipathic peptide which also contains positively charged amino acids because it can interact with DNA as well as with the membrane. Other amino acids in the sequence which can facilitate the delivery are histidines (for endosomal buffering capacity), tryptophan (associated with membrane anchoring property) and serines (can make hydrogen bond and further stabilise the interaction with DNA as well as membrane). The overall hydrophobicity of the peptide should be low while maintaining the amphiphipathicity required for membrane binding because high hydrophobicity is usually associated with cytotoxicity. We then searched primarily the swissprot database for human using HELIQUEST [Gautier R. (2008)] for a target alpha helix forming peptide with these properties. Using sequence statistics and physicochemical parameters we have specifically searched for a peptide possessing the criteria given above.

Amphipathic peptides can be used as carriers of therapeutic biomolecules because they have the potential to overcome cellular barriers encountered in the process of cargo delivery since hydrophobic amino acids can efficiently interact with plasma membrane as well as help in making stable complex with the cargo molecules [Niidome T et al (1999)]. The hydrophilic part of the peptide which is mostly made up of positively charged amino acids can interact with negatively charged cargo molecules and make stable nanocomplexes through non-covalent interactions. The positively charged amino acids like arginine are also known for the ability of cell penetration. However, both the above-mentioned properties have the disadvantage of high cytotoxicity. So the optimisation of these properties in a vector is very important to improve its efficiency. Peptide sequences which presents in human proteins are safer to use and hence designing vectors derived from such sequences is likely to be a better option. Accordingly in the present invention, nanocomplexes are prepared containing different novel amphipathic peptides. A novel peptide system is derived from HUMAN Protein phosphatase 1E (SEQ ID NO:1) and is further modified to generate four more amphipathic peptides to increase transfection efficiency.

The present invention is related to delivery of nucleic acid into the cell while non-covalently complexed with the peptide vector thereby forming a nanocomplex. Nucleic acid delivery encompasses gene delivery, plasmid DNA delivery or small RNA delivery. The peptide length for efficient cellular entry is considered as optimum from 8 to 30 amino acids. But a length less than 18 amino acids cannot make stable alpha helix and the longer length have disadvantage of immunogenicity, synthesis and more. Formation of alpha helix has been considered to be an important feature for an efficient gene delivery system. Hence, further in this invention the peptide length is kept 18 amino acids long which is required for forming alpha helices. Screening of alpha helix forming peptide was done by using the software HELIQUEST. HELIQUEST calculates alpha helix forming propensity of a peptide from its physicochemical properties and amino acid composition and uses the results to screen any databank in order to identify protein segments possessing alpha helix forming peptides. It was found that in some specific environment these peptides have ability to form alpha helix structure. Hence, in this invention the parent peptide length chosen is kept as 18 amino acids long which is required for forming alpha helices (Mgpe-1) (SEQ ID NO:2).

This 18 mer Mgpe peptide (SRLSHLRHHYSKKWHRFR) (SEQ ID NO:2) has 6 positive charges which is then further optimised for better transfection efficiency and reduced cytotoxicity. In the first modification, the total charge of the peptide is increased to 9 replacing three serines with arginines. It has been reported previously that arginines have better cargo interaction property as well as cell penetration ability so further in this invention the two lysines were replaced by arginines and a peptide Mgpe-3 has been generated (RRLRHLRHHYRRRWHRFR) (SEQ ID NO:3).

Amphipatic peptides can be classified in two categories primary and secondary, depending upon the mutual arrangement of the hydrophobic and hydrophilic residues. In primary amphipathic peptides, one terminus has more hydrophobic amino acids and the other consists of more hydrophilic amino acids (e.g., MPG, pep-1, pVEC) but this does not necessarily mean that the respective domains have same hydrophobicity index number [Fernandez-Carneado et al, 2004]. However, in secondary amphipathic peptides, if it adopts alpha helical structure, all the hydrophilic amino acids are arranged on one face of the helix and the hydrophobic amino acids constitute the opposite face (e.g., MAP, KALA, CADY). It is also reported previously that in some cases the transfection efficiency is governed by the amphipaticity of the peptide. Further in this invention, the amphipathicity of the peptide has been changed from secondary (Mgpe-3) to primary amphipathicity by changing the arrangement of amino acids in such a way that all the hydrophobic amino acids are present at N-terminal of the peptide and all hydrophilic amino acids are present at C-terminal of the peptide and a peptide (Mgpe-4) has been generated.

Cysteines have an ability to form disulfide bonds in presence of oxidative environment and these bonds can easily break in reducing environment. This property of cysetine has been used in different polymer systems used for DNA delivery where addition of cysteines helps in strong condensation and protection of the DNA before delivery and allows release of the DNA in the intracellular reducing environment. Thus, cysteines can provide further advantage in terms of condensation release balance as well as anchoring on plasma membrane because mostly the extracellular environment shows oxidative condition whereas intracellular environment has reductive condition [Won Y W et al (2010) and Won Y W et al (2011)]. Therefore, in the present invention further we have incorporated a cysteine residue at each at the end of the peptides Mgpe 3 and Mgpe 4 and generated two peptides Mgpe-9 and Mgpe-10. Peptides have been synthesized by automated solid phase peptide synthesis using Fmoc protected amino acids. The amino acid residues were activated for coupling with HBTU (0-benzotriazole-N,N,N',N',-tetramethyluroniumexafluorophosphate) and HOBt (Nhydroxybenzotriazole) in the presence of DIPEA (diisopropylethylamine). Deprotections were carried out in 2% DBU, 2% piperidine in DMF (N,Ndimethylformamide). Cleavage of the peptide from the resin was performed in Trifluoroacetic acid (TFA), Triisopropylsilane (TIPS) and water. TFA was evaporated and cleavage products dissolved in ether. The water-soluble peptides were extracted with water and lyophilized. Peptides can be purified by reversed phase HPLC, using a C-18 column. The peptide identity was confirmed by MALDI mass spectrometry.

In the present invention, nanocomplexes containing these peptide systems have been generated for efficient transfection with optimum condensation-release balance ability, low cytotoxicity, and efficient endosomal escape property and serum stability of the complexes. The uniqueness of the systems is that these peptides are novel for cargo delivery and further optimized for best transfection efficiency. These systems show better transfection efficiency than commonly used commercial transfection agents and show very less cytotoxicity and are easy to synthesize as well.

The aim of the invention is to provide a simple and efficient way to achieve high transfection efficiency. Non-covalent attachment of the cargo to the vector through formation of nanocomplex has been used for preparing the delivery formulation. This is not only the simple way but also has enormous possibility of the different combinations which can be tried to arrive at the best transfection efficiency. In this invention nanocomplexes were prepared at different charge ratios expressed as peptide nitrogen per nucleic acid phosphate (N/P), i.e. Z (+/−). The nucleic acid stock was diluted to an appropriate concentration and added drop-wise to an equal volume of the appropriate peptide dilution while vortexing. The nanocomplexes were incubated for 30 min or 1 h at room temperature before performing any experiment.

The ability of the peptide to make nanocomplex with plasmid DNA was checked by measuring the electrophoretic mobility of the nanocomplexes at different charge ratios. The amount of the DNA in each sample was kept same and the amount of the peptide was varied in each case. The electrophoretic mobility of the nanocomplexes at different charge ratios was studied using agarose gel electrophoresis. 20 µl of the nanocomplex having 200 ng of plasmid DNA was loaded in each case onto 1% agarose gel containing ethidium bromide. Electrophoresis was carried out at 135 V in 1×TAE buffer (pH 7.4) for 30 min. Lane 1-Ctrl (only plasmid DNA), Lane 2-9 are the nanocomplexes formed at different charge ratios (0.5-10). The following figures represent the results of agarose gel electrophoresis: FIG. 1A for Mgpe-1 (SEQ ID NO:2), FIG. 1B for Mgpe-3, FIG. 1C for Mgpe-4, FIG. 1D for Mgpe-9 and FIG. 1E for Mgpe-10.

Interaction of the peptide with DNA leading to DNA condensation was also measured by the inhibition of DNA-intercalated EtBr fluorescence signal in the presence of peptides. Intercalation of EtBr into free DNA increases the fluorescence of EtBr and gives 10 fold greater fluorescence emission. DNA binding peptide excludes EtBr from the DNA due to nanocomplexes formation, resulting in decrease in fluorescence intensity of EtBr. This drop can be used as a measure of peptide-DNA interaction as well as DNA condensation. The assay was carried out in black 96-well format plates (Nunc) where 4.22 µl EtBr (10 ng/µl) and 20 µl DNA (20 ng/µl) was dispensed in each well and incubated in dark for 5 min at room temperature. 20 µl of peptide solution at increasing charge ratio was then added to the wells and the plate incubated for another 10 min in dark. Fluorescence was measured in DTX 880 Multimode detector (Beckman Coulter) using 535 SL EXP 1 excitation and 595 SL EMP 1 emission filters. The fluorescence of only DNA with EtBr was taken as the maximum, i.e. 100% and the relative percentage decrease in fluorescence signal was calculated at increasing charge ratio of peptide to DNA and plotted as percentage of maximum (% of Max). In the present invention, the peptides were able to condense large plasmid DNA non-covalently and efficiently to form nanocomplexes. The following Figures show the results of EtBr intercalation assay: FIG. 3A for Mgpe-1 (SEQ ID NO:2), FIG. 3B for Mgpe-3, FIG. 3C for Mgpe-4, FIG. 3D for Mgpe-9 and FIG. 3E for Mgpe-10.

It is very important that the cargo forms stable nanocomplexes with the peptide but simultaneously it must also be sufficiently loosely packaged so that the nanocomplex can be disassembled inside the cell. Hence, the balance of efficient DNA condensation and intracellular release is an important parameter in governing the DNA delivery efficiency. When the nanocomplex encounters an anionic challenge like heparin, the positively charged peptide interacts with the anionic agent, destabilizes the complex and releases DNA. Nanocomplexes were prepared with peptide and plasmid DNA at Z (+/−) of 10 and incubated for 30 min at room temperature. The nanocomplexes were treated with increasing amount of anionic agent heparin (H3149-100KU) in wt/wt (heparin/peptide) ratios ranging from 0.1:1 to 3:1, incubated for a further 30 min at room temperature again and run on 1% agarose gel. The amount of the DNA released from the nanocomplexes was compared with the control here which is bare DNA. FIG. 2 shows DNA release from the nanocomplexes at different Wt/Wt ratios of heparin:petideDNA release assay. Lane 1-Ctrl (only plasmid DNA), Lane 2-10 are different weight/weight ratios of heparin/peptide (0.0-3.0). The following Figures show the results of the gel release assay: FIG. 2A for Mgpe-1 (SEQ ID NO:2), FIG. 2B for Mgpe-3 (SEQ ID NO:3), FIG. 2C for Mgpe-4 (SEQ ID NO:4), FIG. 2D for Mgpe-9 (SEQ ID NO:5) and FIG. 2E for Mgpe-10 (SEQ ID NO:6).

The stability of the nanocomplexes was also checked with EtBr assay. Heparin at increasing amounts was added to black 96 well plates (Nunc), followed by addition of 20 µl of nanocomplexes (which was made 30 min before) and 10 µlEtBr (4.22 ng/µl) and incubated for 15 min at room temperature in the dark. The fluorescence of only DNA with EtBr was taken as 100% and the relative percentage fluorescence signal was calculated at increasing concentration of heparin. The following Figures show the results of the DNA release assay: FIG. 4A for Mgpe-1, FIG. 1B for Mgpe-3, FIG. 4C for Mgpe-4, FIG. 4D for Mgpe-9 and FIG. 4E for Mgpe-10.

The mean hydrodynamic diameter and zeta potential of nanocomplexes prepared at charge 10.0 at 25 ng/µl of DNA concentration in deionized water were measured by Zeta sizer Nano ZS (Malvern Instruments, UK) at a fixed angle of 173° at 25° C. Minimum of 3 readings were recorded for each sample with replicates. As presented in Table-2 all the peptides were able to make nanocomplexes with DNA. The size of nanocomplexes was ranging from 50 to 110 nm and Zeta potential was ranging from 30 to 60 mV.

The transfection efficiency in terms of reporter gene expression has been checked using luciferase reporter assay. A plasmid (pMIR-Report™ Luciferase) containing luciferase gene was complexed with the peptide and transfected to the cell. The nanocomplexes were made at different charge ratios and transfected in a wide range of cell lines. CHO-K1 cells were maintained in Ham's F-12K media and MCF-7 and A549 cells in low glucose DMEM supplemented with 10% (v/v) Fetal bovine serum (Life Technologies, USA); at 37° C. and 5% CO2 in humidified incubator. Cells were seeded 24 h before transfection in 24-well plates. Nanocomplexes were prepared with final DNA concentration of 20 ng/µl and incubated for 1 h at room temperature. 100 µl of nanocomplex was added to cells at ~70% confluency in serum-free media (OptiMEM, Invitrogen). After 5 h of incubation at 37° C. and 5% CO2 in humidified incubator, the media was aspirated; cells were washed with phosphate buffered saline (PBS, pH 7.4) and supplemented with 500 µl of complete growth medium. After 24 h, cells were washed with PBS and lysed with 100 µl of cell culture lysis buffer (1×CCLR, Promega). Luciferase expression was measured in 50 µl of cell lysate supernatant using the luciferase assay substrate (Promega). Light emission was measured by integration over 1 Os in Orion microplate luminometer (Berthold Detection System, Germany). Luciferase activity was normalized with total protein content of the cells estimated using BCA protein assay (Pierce).

All the five peptides showed good transfection efficiency of plasmid DNA in CHO-K1 cells while non-covalently complexed. Nanocomplexes of Mgpe-3 and Mgpe-4 showed higher or equal transfection efficiency to the commercially available agent Cellfectin and Superfect in CHO-K1 cells at charge ratio 10 and 5 respectively whereas Mgpe-9 showed highest transfection efficiency, higher Cellfectin and Superfect and equal to Lipofectamine2000 at charge ratio 5.

To check the effect of chloroquine, cells were treated with 100 µM final concentration of chloroquine with nanocomplex for 5 h. After 24 h the expression of the reporter gene was measured as mentioned above. Here presence of chloroquine did not have any big difference in transfection efficiency indicating these peptides in the nanocomplexes have inherent property to come out of the endosomal barrier.

To check the universality of these transfection systems, transfection was carried out in many cell lines which are from different origin like CHO-K1, MCF-7 and A549. These peptides showed promising transfection efficiency in all the cell lines checked.

In order to evaluate the stability of the nanocomplexes against serum, we performed the Serum Stability Assay. The nanocomplexes were prepared by mixing of peptides with DNA (20 ng/µl) at the charge ratio of 10 and incubated at room temperature for 30 min. The respective percentage of serum was added and the nanocomplexes were incubated at 37° C. for 2 h after which the reaction tubes were kept at 75° C. for 15 min to deactivate serum nucleases and proteases. Heparin (w/w ratio-5:1) was added in the respective tubes and further incubated at 37° C. for 15 min after that sample were run on 1% agarose gel.

In order to evaluate the transfection in presence of serum MCF-7 cells were seeded 24 h before transfection. After 24 h transfections have been done at charge ratio 10, 20 and 30 for Mgpe-3, Mgpe-4 and Mgpe-9. Nanocomplexes were prepared with final DNA concentration of 20 ng/µl and incubated for 1 h at room temperature. 100 µl of nanocomplex was added to cells at ~70% confluency in complete media (having 10% serum). After 5 h of incubation at 37° C. and 5% CO2 in humidified incubator, the media was aspirated; cells were supplemented with 500 µl of fresh medium. After 24 h the expression of the reporter gene was measured as mentioned above.

Nanocomplexes with these peptides did not show any cytotoxicity at charge ratios used in transfection. They showed less toxicity in comparison to the commercially available agent Lipofectamine2000. Cell viability was evaluated using CellTiter-Glo® Luminescent Cell Viability Assay (Promega). The CellTiter-Glo® Luminescent Cell Viability Assay is a homogeneous method to determine the number of viable cells in culture based on quantitation of the ATP present. Briefly, CHO-K1 cells were seeded 1 day before treatment into 96-well plate. Cells were treated with a 20 µl of nanocomplexes made at charge ratio 10 in serum-free media for 5 h, the media was aspirated and supplemented with 100 µl complete growth medium. Thereafter, cell viability was evaluated according to the manufacturer's protocol. Untreated cells were defined as 100% viable in cell viability assay.

The uptake of the small RNA, which is noncovalently complexed with the peptides, was almost 100% in CHO-K1 cells at charge ratio 5 for Mgpe-9 and Mgpe-10. Siglo was used as a model small RNA. This RNA was used to prepare the nanocomplexes with the peptide at charge ratio 5.0. Chinese hamster ovary cells (CHO-K1) were maintained in Ham's F-12K media supplemented with 10% (v/v) Fetal bovine serum (Life Technologies, USA); at 37° C. and 5%

CO2 in humidified incubator. Cells were grown in 24 well plate which was seeded 24 h before use. At a confluency of 70-80% the cells were treated with labelled nanocomplexes for 4 h at 37° C. After incubation, the media was removed and cells were washed twice with PBS supplemented with heparin (1 mg/ml). The cells were then treated with trypsin (0.25%) for 5-10 min and harvested in complete media, pelleted down, washed with PBS, resuspended in PBS having 1% BSA and then analyzed on FACS-Calibur™ (Becton Dickinson, USA) using CellQuest. Pro software. The labelled nanocomplexes were excited using 488 nm laser and detected with 530/30 nm (FL1) band pass filter. In each case total 10,000 events were acquired. Percentage of fluorescence positive cells was plotted as bars and their mean intensity was plotted as a line. Both the nanocomplexes showed delivery of small RNA very efficiently.

EXAMPLES

The following examples are given by way of illustration therefore should not be constructed to limit the scope of the Invention.

Example 1

Identifying Peptide Sequence of Human Protein Phosphatase 1E

Screening an alpha helix forming peptide software HELI-QUEST was used. HELIQUEST calculates alpha helix forming propensity of a peptide from its physicochemical properties and amino acid composition and uses the results to screen any databank in order to identify protein segments possessing alpha helix forming peptides. Screening α-Helix allows the user to screen SwissProt databases or any personal databases in order to find sequences that have the general physico-chemical features of an alpha helix sequence. In HeliQuest, required physicochemical property needed to search a peptide in a database can be given. There was one peptide Human Protein phosphatase 1E (SEQ ID NO:1) that satisfied the criteria. The 18 mer Mgpe-1 peptide (SRLSHLRHHYSKKWHRFR) (SEQ ID NO:2) has 6 positive charges which is then further optimised for better transfection efficiency and reduced cytotoxicity.

Example 2

Preparation of Mgpe Mutants

In the first modification, the total charge of the peptide is increased to 9 by replacing three serines with arginines. The peptide so generated is named as Mgpe3 and the sequence of the peptide so obtained is (RRLRHLRHHYRRWHRFR) (SEQ ID NO:3). Further in this invention, the amphipathicity of the peptide has been changed from secondary (Mgpe-3) to primary amphipathicity by changing the arrangement of amino acids in such a way that all the hydrophobic amino acids are present at N-terminal of the peptide and all hydrophilic amino acids are present at C-terminal of the peptide and a peptide Mgpe-4 with sequence (LLYWFRRRHRHHRRRHRR) (SEQ ID NO:4) is generated.

The peptide Mgpe 3 and Mgpe 4 were further modified by incorporating cysteine residue at each end of the peptides Mgpe 3 and Mgpe4 to generate peptides Mgpe-9 (CRRLRHLRHHYRRRWHRFRC) (SEQ ID NO:5) and Mgpe-10 (CLLYWFRRRHRHHRRRHRRC) (SEQ ID NO:6) respectively. The sequences of the peptides prepared are mentioned in the Table 1.

| NAME OF PEPTIDE | AMINO ACID SEQUENCE | SEQUENCE ID NO. |
|---|---|---|
| Mgpe-1 | SRLSHLRHHYSKKWHRFR | 2 |
| Mgpe-3 | RRLRHLRHHYRRWHRFR | 3 |
| Mgpe-4 | LLYWFRRRHRHHRRRHRR | 4 |
| Mgpe-9 | CRRLRHLRHHYRRRWHRFRC | 5 |
| Mgpe-10 | CLLYWFRRRHRHHRRRHRRC | 6 |

Example 3

Synthesis of Nanocomplexes

The aim of the invention is to provide a simple and efficient way to achieve high transfection efficiency. Non-covalent attachment of the cargo to the Mgpe peptides through formation of nanocomplex has been used for preparing the delivery formulation. This is not only the simple way but also has enormous possibility of the different combinations which can be tried to arrive at the best transfection efficiency. In the present invention, nanocomplexes were prepared at different charge ratios expressed as peptide nitrogen per nucleic acid phosphate (N/P), i.e. Z (+/−). The nucleic acid stock was diluted to an appropriate (20-50 ng/μl) concentration and added drop-wise to an equal volume of the appropriate (10-100 μl) peptide dilution while vortexing. The nanocomplex was incubated for 30 min or 1 h at room temperature before performing any experiment.

Example 4

Gel Retardation Assay

The ability of the peptides to make nanocomplex with plasmid DNA was checked by measuring the electrophoretic mobility of the nanocomplexes at different charge ratios. The amount of the DNA in each sample was kept same and the amount of the peptide was varied in each case. The electrophoretic mobility of the nanocomplexes at different charge ratios was studied using agarose gel electrophoresis. 20 μl of the nanocomplex having 200 ng of plasmid DNA was loaded in each case onto 1% agarose gel containing ethidium bromide. Electrophoresis was carried out at 135 V in 1×TAE buffer (pH 7.4) for 30 min. All the invented peptides condensed the DNA efficiently and formed nanocomplex. In order to analyze the stability of nanocomplexes against anionic challenge, nanocomplexes were prepared with peptide and plasmid DNA at Z (+/−) of 10 and incubated for 30 min at room temperature. The nanocomplexes were treated with increasing amount of anionic agent heparin (H3149-100KU) wt/wt (heparin/peptide) in the ratio of 0.1:1 to 3:1, incubated for a further 30 min at room temperature again and run on 1% agarose gel. The amount of the DNA released from the nanocomplexes was compared with the control here which is bare DNA. Nanocomplex of all the invented peptides showed efficient stability in presence of anionic challenge.

Example 5

EtBr Exclusion Assay

Intercalation of EtBr into free DNA increases the fluorescence of EtBr and gives 10 fold greater fluorescence emission. DNA binding peptide excludes EtBr from the DNA due to nanocomplex formation, resulting in decrease in fluorescence intensity of EtBr. This drop can be used as a measure of peptide-DNA interaction as well as DNA condensation. The assay was carried out in black 96-well format plates (Nunc) where 4.22 μlEtBr (10 ng/μl) and 20 μl DNA (20 ng/μl) was dispensed in each well and incubated in dark for 5 min at room temperature. 20 μl of peptide solution at increasing charge ratio was then added to the wells and the plate incubated for another 10 min in dark. Fluorescence was measured in DTX 880 Multimode detector (Beckman Coulter) using 535 SL EXP 1 excitation and 595 SL EMP 1 emission filters. The fluorescence of only DNA with EtBr was taken as the maximum, i.e. 100% and the relative percentage decrease in fluorescence signal was calculated at increasing charge ratio of peptide to DNA and plotted as percentage of maximum (% of Max). All the invented peptides condensed the DNA efficiently and formed nanocomplex.

For nanocomplex stability study, heparin was added to 96 well plates (Nunc) at increasing amounts, followed by addition of 20 μl of nanocomplex prepared at charge ratio 10 and 10 μl EtBr (4.22 ng/μl) and incubated for 15 min at room temperature in the dark. The fluorescence of DNA with EtBr was taken as 100% and the relative percentage increase in fluorescence signal was calculated at increasing concentration of heparin. Fluorescence was measured in DTX 880 Multimode detector (Beckman Coulter) using 535 SL EXP 1 excitation and 595 SL EMP 1 emission filters. Nanocomplex of all the invented peptides showed efficient stability in presence of anionic challenge.

Example 6

Determination of Size and Zeta Potential of Nanocomplexes by DLS

The mean hydrodynamic diameter and zeta potential of nanocomplex (Table 2) prepared at charge 10 at 25 ng/μl of DNA concentration in deionized water were measured by Zeta sizer Nano ZS (Malvern Instruments, UK) at a fixed angle of 173° at 25° C. Minimum of 3 readings were recorded for each sample with replicates. All five invented peptides were able to Make monodisperse nanocomplex with sizes ranging from 50 nm to 110 nm with DNA.

TABLE 2

Size (nm), PDI and Zeta potential (mV) of the nanocomplexes at charge ratio 10. Final concentration of DNA was 25 ng/μl.

| NAME OF PEPTIDE | Size (nm) | PDI | Zeta potential (mV) |
|---|---|---|---|
| Mgpe-1 | 80.1 ± 7.3 | 0.151 ± 0.031 | 36.5 ± 0.8 |
| Mgpe-3 | 63.2 ± 4.5 | 0.152 ± 0.014 | 33.5 ± 5.9 |
| Mgpe-4 | 62.8 ± 7.0 | 0.155 ± 0.010 | 25.4 ± 0.2 |
| Mgpe-9 | 75.8 ± 3.8 | 0.169 ± 0.002 | 43.4 ± 0.1 |
| Mgpe-10 | 66.2 ± 0.7 | 0.206 ± 0.004 | 57.6 ± 3.2 |

Example 7

Transfection Efficiency Measurement Using Luciferase Assay

CHO-K1 cells were maintained in Ham's F-12K media and MCF-7 and A549 cells in low glucose DMEM supplemented with 10% (v/v) Fetal bovine serum (Life Technologies, USA); at 37° C. and 5% CO2 in humidified incubator. Cells were seeded 24 h before transfection in 24-well plates. A plasmid (pMIR-Report™ Luciferase) containing luciferase gene was complexed with the peptide and transfected to the cell. The nanocomplexes were made at different charge ratios and transfected in a wide range of cell lines. Nanocomplexes were prepared with final DNA concentration of 20 ng/μl and incubated for 1 h at room temperature. 100 μl of nanocomplex was added to cells at 70% confluency in serum-free media (OptiMEM, Invitrogen). Cellfectin, Superfect and Lipofectamine2000 used as manufacturer protocol. In case of transfection in presence of serum, nanocomplexes were added in complete media. After 5 h of incubation at 37° C. and 5% CO2 in humidified incubator, the media was aspirated; cells were washed with phosphate buffered saline (PBS, pH 7.4) and supplemented with 500 μl of complete growth medium. To check the effect of chloroquine, cells were treated with 100 μM final concentration of chloroquine with nanocomplex for 5 h. After 24 h, cells were washed with PBS and lysed with 100 μl of cell culture lysis buffer (1×CCLR, Promega). Luciferase expression was measured in 50 μl of cell lysate supernatant using the luciferase assay substrate (Promega). Light emission was measured by integration over 10 s in Orion micro plate luminometer (Berthold Detection System, Germany). Luciferase activity was normalized with total protein content of the cells estimated using BCA protein assay (Pierce). Nanocomplex containing all five invented peptides showed transfection efficiency of 7-9 orders in RLU/mg protein.

TABLE 3

Cell lines deposition details

| Name | ATCC Number |
|---|---|
| CHO-K1 | CCL-61 |
| MCF-7 | HTB-22 |
| A549 | CCL-185 |

Example 8

Transfection Efficiency in Presence of Chloroquine

Figure 6:
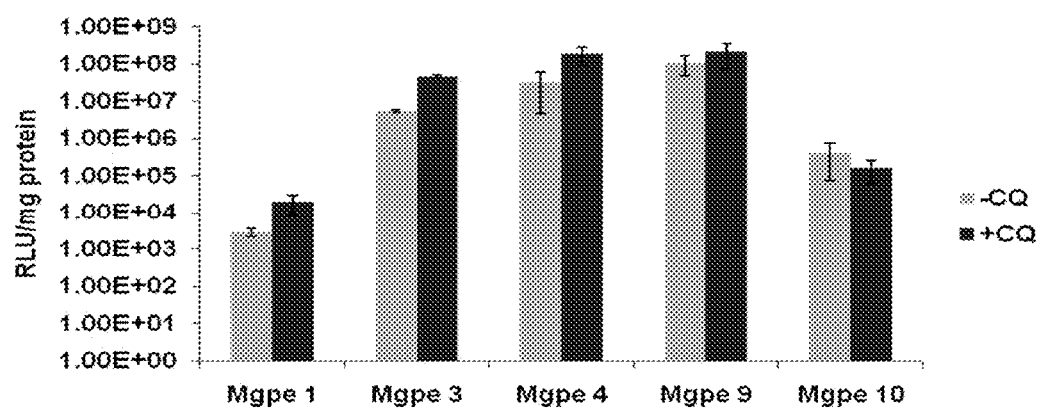
FIG. 6 shows transfection efficiency; in vitro transfection of the luciferase gene into CHO-K1 in absence and in presence of 100 µM chloroquine (CQ). Transfections have been done at charge ratio 10 for Mgpe-1 (SEQ ID NO:2) and Mgpe-3 and at charge ratio 5 for Mgpe-4, Mgpe-9 and Mgpe 10. Cells were incubated with the nanocomplexes for 5 h and luciferase activity was measured after 24 h.
Figure 7:
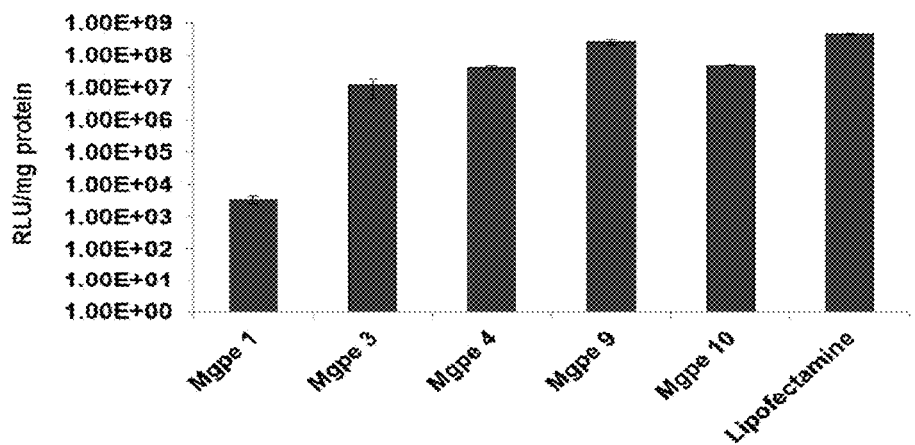
FIG. 7 shows in vitro transfection of the luciferase gene into different cells; (A) MCF-7, (B) A549 by different nanocomplexes in the different conditions as mentioned above. Cells were incubated with the nanocomplexes for 5 h and luciferase activity was measured after 24 h.
Figure 7:
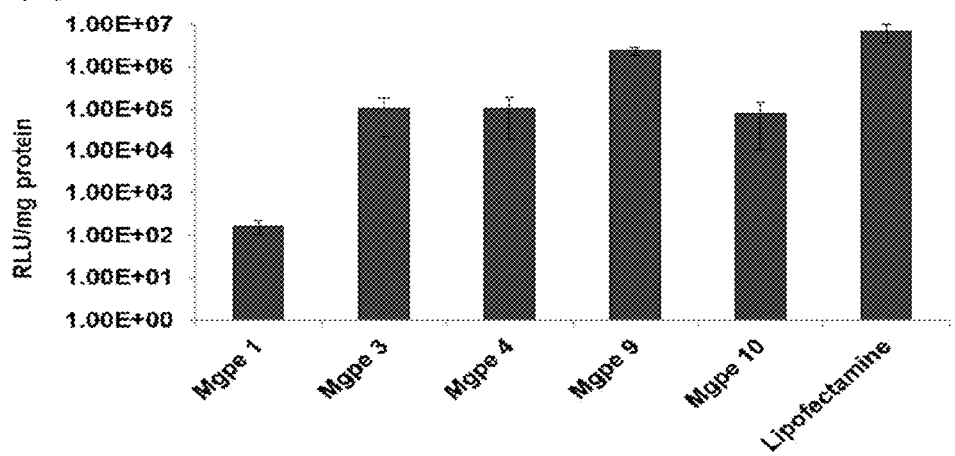

To check the effect of chloroquine, cells were treated with 100 μM final concentration of chloroquine with nanocomplexes for 5 h prepared at charge ratio ranging from 3 to 50 after which the expression of the reporter gene was measured as mentioned above. The results for this assay are shown in FIG. 6. The presence of chloroquine did not have any big difference in transfection efficiency indicating these peptides have inherent property to come out of the endosomal barrier.

Example 9

Transfection of Luciferase Gene into Multiple Cell Lines

The transfection efficiency in terms of reporter gene expression has been checked using luciferase reporter assay.

A plasmid (pMIR-Report™ Luciferase) containing luciferase gene was complexed with the peptide and transfected to the cell. The nanocomplexes were made at different charge ratios and transfected in a wide range of cell lines. CHO-K1 cells were maintained in Ham's F-12K media and MCF-7 and A549 cells in low glucose DMEM supplemented with 10% (v/v) Fetal bovine serum (Life Technologies, USA); at 37° C. and 5% CO2 in humidified incubator. Cells were seeded 24 h before transfection in 24-well plates. Nanocomplexes were prepared with final DNA concentration of 20 ng/µl and incubated for 1 h at room temperature. 100 µl of nanocomplex was added to cells at ~70% confluency in serum-free media (OptiMEM, Invitrogen). After 5 h of incubation at 37° C. and 5% CO2 in humidified incubator, the media was aspirated; cells were washed with phosphate buffered saline (PBS, pH 7.4) and supplemented with 500 µl of complete growth medium. After 24 h, cells were washed with PBS and lysed with 100 µl of cell culture lysis buffer (1×CCLR, Promega). Luciferase expression was measured in 50 µl of cell lysate supernatant using the luciferase assay substrate (Promega). Light emission was measured by integration over 10 s in Orion micro plateluminometer (Berthold Detection System, Germany). Luciferase activity was normalized with total protein content of the cells estimated using BCA protein assay (Pierce). Nanocomplex containing all five invented peptides showed transfection efficiency of 7-9 orders in RLU/mg protein in multiple cell lines.

Example 10

Serum Stability Assay

In order to evaluate the stability of the nanocomplexes against serum, Serum Stability Assay was performed. The nanocomplexes were prepared by mixing of peptides with DNA (20 ng/µl) charge ratio 10 containing 200 ng of DNA and incubated at 25° C. for 30 min. The respective percentages of serum were added and the nanocomplexes were incubated at 37° C. for 2 h after which the reaction tubes were kept at 75° C. for 15 min to deactivate serum nucleases and proteases. Heparin (w/w ratio-5:1) was added in the respective tubes and further incubated at 37° C. for 15 min after that sample were run on 1% agarose gel. The results are given in FIG. 8. Nanocomplex containing invented peptides showed protection of biomolecules in presence of serum.

Example 11

Transfection in Presence of Serum

In order to evaluate the transfection in presence of serum MCF-7 cells were seeded 24 h before transfection. After 24 h transfections have been done at charge ratio 10, 20 and 30 for Mgpe-3, Mgpe-4 and Mgpe-9. Nanocomplexes were prepared with final DNA concentration of 20 ng/µl and incubated for 1 h at room temperature. 100 µl of nanocomplex was added to cells at ~70% confluency in complete media (having 10% serum). After 5 h of incubation at 37° C. and 5% CO2 in humidified incubator, the media was aspirated; cells were supplemented with 500 µl of fresh medium. After 24 h the expression of the reporter gene was measured as mentioned above. The results are given in FIG. 9. Nanocomplex containing invented peptides showed efficient transfection in eukaryotic cells in serum containing medium.

Example 12

Luminescent Cell Viability Assay

Figure 10:
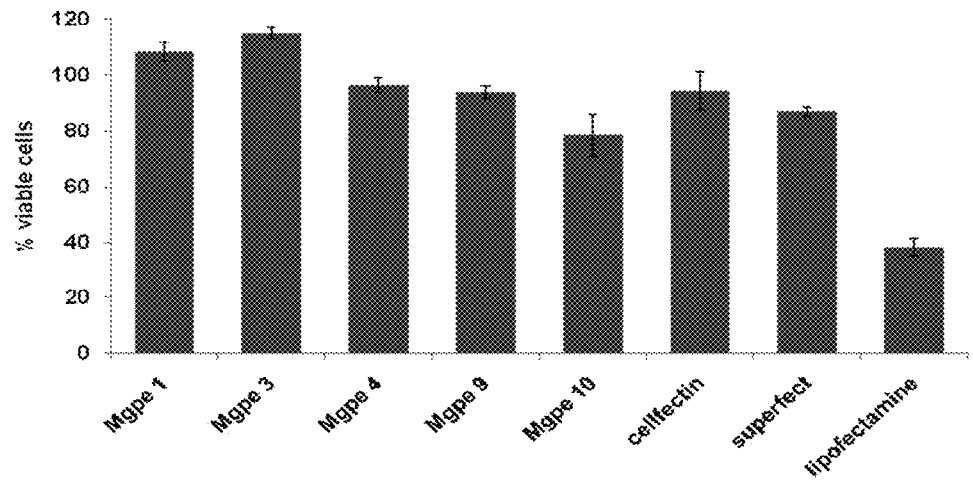
FIG. 10 shows cell viability assay: cell viability in presence of nanocomplexes at charge ratio 10 for Mgpe-1 (SEQ ID NO:2) and Mgpe-3 and at charge ratio 5 for Mgpe-4, Mgpe-9 and Mgpe-10 was evaluated using CellTiter-Glo® Luminescent Cell Viability Assay after 24 h in CHO-K1 cells. Untreated cells were defined as 100% viable.

The CellTiter-Glo® Luminescent Cell Viability Assay is a homogeneous method to determine the number of viable cells in culture based on quantitation of the ATP present. Briefly, CHO-K1 cells were seeded 1 day before treatment into 96-well plate. At 70-80% confluency cells were treated with a 20 µl of nanocomplexes at charge ratio 10 in serum-free media for 5 h, the media was aspirated and supplemented with 100 µl complete growth medium. These peptides did not show any cytotoxicity at charge ratios used in transfection. Thereafter, cell viability was evaluated according to the manufacturer's protocol. Untreated cells were defined as 100% viable in cell viability assay. These nanocomplexes showed less toxicity in comparison to the commercially available agent Lipofectamine2000. Cell viability was evaluated using CellTiter-Glo® Luminescent Cell Viability Assay (Promega). The results are given in FIG. 10. Nanocomplex containing all five invented peptides showed high transfection efficiency with minimal cytotoxicity.

Example 13

Cellular Uptake of RNA

Figure 11:
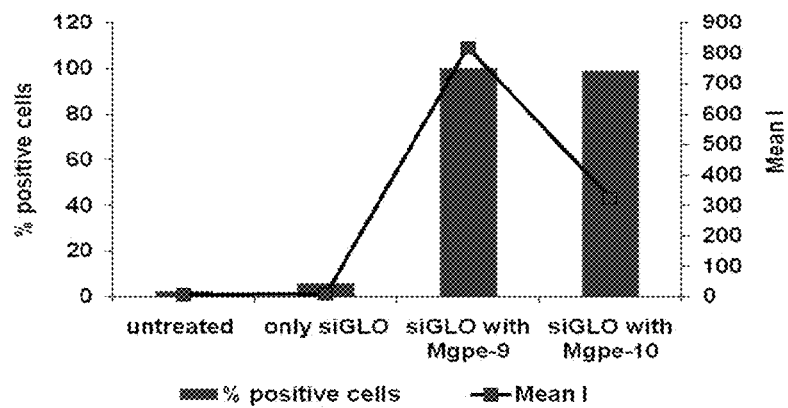
FIG. 11 shows cellular uptake of the nanocomplexes (siglo and peptide); Percentage of fluorescence positive cells (bars) and their mean intensity (line) measured using flow cytometry after 4 h incubation with the nanocomplexes formed using Mgpe-9 and Mgpe-10 at charge ratio 5 in CHO-K1 cells (where the RNA is labelled with FITC).

Siglo was used as a model small RNA This RNA was used to prepare the nanocomplexes with the peptide at charge ratio 5.0. Chinese hamster ovary cells (CHO-K1) were maintained in Ham's F-12K media supplemented with 10% (v/v) Fetal bovine serum (Life Technologies, USA); at 37° C. and 5% CO2 in humidified incubator. Cells were grown in 24 well plates which was seeded 24 h before use. At a confluency of 70-80% the cells were treated with labelled nanocomplexes for 4 h at 37° C. After incubation, the media was removed and cells were washed twice with PBS supplemented with heparin (1 mg/ml). The cells were then treated with trypsin (0.25%) for 5-10 min and harvested in complete media, pelleted down, washed with PBS, resuspended in PBS having 1% BSA and then analyzed on FACS-Calibur™ (Becton Dickinson, USA) using CellQuest Pro software. The labelled nanocomplexes were excited using 488 nm laser and detected with 530/30 nm (FL1) band pass filter. In each case total 10,000 events were acquired. Percentage of fluorescence positive cells was plotted as bars and their mean intensity was plotted as a line. The uptake of the small RNA, which is noncovalently complexed with the peptides, was almost 100% in CHO-K1 cells at charge ratio 5 for Mgpe-9 and Mgpe-10. Both the peptides showed delivery of small RNA very efficiently. The results are given in FIG. 11. Nanocomplex containing invented peptide can carry biomolecules in the range of 20 bp to 7 kbp size.

Advantages of the Invention

1. The peptides in the nanocomplex are easy to synthesise.
2. The attachment of the cargo to the peptides is non-covalent which is a very simple process and gives enormous possibility of combinations.
3. These peptide systems can non-covalently complex small and large biomolecules like DNA and RNA.

4. These nanocomplexes are able to carry large cargo like plasmid DNA inside the cell.
5. It has the ability to transfect a variety of cell line systems which can be from different origin such as CHO-K1, MCF-7 and A549.
6. These systems show higher or equal transfection efficiency in comparison with liposomal and PEI based commercial transfection agent like Cellfectine, Superfect and Lipofectamine 2000.
7. Transfection efficiency of these systems is not increased in presence of chloroquine indicating these systems have an ability to escape endosomal barrier which is very advantageous in delivering the biomolecules.
8. These nanocomplexes have an ability to protect the cargo from serum degradation which is advantageous in terms of in vivo delivery.
9. These system shows transfection even in presence of serum.
10. The nanocomplexes carry negligible cytotoxicity compared to other known commercial transfection agents.
11. These systems also are able to deliver small RNA into the cell while complexed noncovalently.

REFERENCES

Edelstein M L, Abedi M R, Wixon J (2007) Gene therapy clinical trials worldwide to 2007—an update. J Gene Med. 9:833-842

Meredith A. Mintzer, Eric E. Simanek, Nonviral Vectors for Gene Delivery, Chem. Rev. 109 (2), (2009) 259-302

Niidome T and Huang L, Gene Therapy Progress and Prospects: Nonviral vectors, Gene Therapy (2002) 9, 1647-1652

Mintzer M A, Simanek E E. Nonviral vectors for gene delivery. Chem Rev. 2009; 109: 259-302.

Remaut K, Sanders N N, De Geest B G, Braeckmans K, Demeester J, De Smedt S C. Nucleic acid delivery: Where material sciences and bio-sciences meet. Mater. Sci. Eng., R. 2007; 58: 117-161.

Liu D, Ren T, Gao X. (2003) Cationic transfection lipids. Curr Med Chem. 10:1307-1315

Fischer D, Li Y, Ahlemeyer B, Krieglstein J, Kissel T. In vitro cytotoxicity testing of polycations: influence of polymer structure on cell viability and hemolysis. Biomaterials. 2003 March; 24(7):1121-31.

Fabre, J. W. and Collins, L. (2006) Synthetic Peptides As Non-Viral Dna Vectors. Curr. Gene Ther. 6, 459-480

Fernandez-Carneado J, Kogan M J, Pujals S, Giralt E, Amphipathic Peptides and Drug Delivery, Biopolymers (Peptide Science) 76, (2004) 196-203

Fominaya J, Gasset M, Garcia R, Roncal F, Albar J P, Bernad A., An optimized amphiphilic cationic peptide as an efficient non-viral gene delivery vector, J Gene Med. 2 (2000) 455-464.

Kuriyama S, Taguchi Y, Nishimura K, Mizuguchi K, Kobayashi K, Katayama Y, Yanagibashi K, Niidome T. Peptide vector for gene delivery with high affinity for Phosphatidylserine, J Pept Sci. 12 (2006) 626-32.

Bartz R, Fan H, Zhang J, Innocent N, Cherrin C, Beck S C, Pei Y, Momose A, Jadhav V, Tellers D M, Meng F, Crocker L S, Sepp-Lorenzino L, Barnett S F. Effective siRNA delivery and target mRNA degradation using an amphipathic peptide to facilitate pH-dependent endosomal escape, Biochem. J. 435 (2011) 475-487

Oehlke J, Wallukat G, Wolf Y, Ehrlich A, Wiesner B, Berger H, Bienert M, Enhancement of intracellular concentration and biological activity of PNA after conjugation with a cell-penetrating synthetic model peptide. Eur. J. Biochem. 271 (2004) 3043-3049

Niidome T, Urakawa M, Sato H, Takahara Y, Anai T, Hatakayama T, Wada A, Hirayama T, Aoyagi H, Gene transfer into hepatoma cells mediated by galactose-modified a-helical peptides, Biomaterials 21 (2000) 1811-1819

Elmquist A, Lindgren M, Bartfai T, Langel U. Vecadherin-derived cell-penetrating peptide, pVEC with carrier functions, Experimental Cell Research. 269 (2001) 237-244.

Wyman T B, Nicol F, Zelphati O, Scaria P V, Plank C, Szoka F C Jr. Design, synthesis, and characterization of a cationic peptide that binds to nucleic acids and permeabilizes bilayers, Biochemistry 36 (1997) 3008-3017.

Rajpal, Mann A, Khanduri R, Naik R J, Ganguli M. Structural rearrangements and chemical modifications in known cell penetrating peptide strongly enhance DNA delivery efficiency J Control Release. 2012 Jan. 30; 157(2):260-71

Mann A, Thakur G, Shukla V, Singh A K, Khanduri R, Naik R, Jiang Y, Kalra N, Dwarakanath B S, Langel U, Ganguli M. Differences in DNA condensation and release by lysine and arginine homopeptides govern their DNA delivery efficiencies. Mol Pharm. 2011 Oct. 3; 8(5):1729-41

Niidome T, Ohmori N, Ichinose A, Wada A, Mihara H, Hirayama T, Aoyagi H. Binding of cationic alpha-helical peptides to plasmid DNA and their gene transfer abilities into cells. J Biol Chem. 1997 Jun. 13; 272(24):15307-12.

Niidome T, Urakawa M, Takaji K, Matsuo Y, Ohmori N, Wada A, Hirayama T, Aoyagi H. Influence of lipophilic groups in cationic alpha-helical peptides on their abilities to bind with DNA and deliver genes into cells. J Pept Res. 1999 October; 54(4):361-7.

Gautier R., Douguet D., Antonny B. and Drin G. HELIQUEST: a web server to screen sequences with specific α-helical properties. Bioinformatics. 2008 Sep. 15; 24(18):2101-2.

Won Y W, Kim H A, Lee M, Kim Y H. Reducible Poly (oligo-D-arginine) for enhanced gene expression in mouse lung by intratracheal injection. Mol. Ther. 2010; 18: 734-742.

Won Y W, Yoon S M, Lee K M, Kim Y H. Poly (oligo-D-arginine) with internal disulfide linkages as a cytoplasm sensitive carrier for siRNA delivery. Mol. Ther. 2011; 19: 372-380.

We claim:

1. A nanocomplex useful for efficient transfection comprising the amino acid sequence SEQ ID NO:3, SEQ ID NO:4, SEQ ID NO:5 or SEQ ID NO:6.

2. The nanocomplex as claimed in claim 1, wherein the sequence is an amphipathic human protein phosphatase 1E (Mgpe) peptide consisting of SEQ ID NO:3, SEQ ID NO:4, SEQ ID NO:5 or SEQ ID NO:6 where Mgpe peptide is a peptide which is having the amino acid similarity with a segment of Human protein phosphatase 1E from 665 amino acids to 682 or a modified derivative of SEQ ID NO:3, SEQ ID NO:4, SEQ ID NO:5 or SEQ ID NO:6.

3. The nanocomplex as claimed in claim 1, wherein the peptide is operably linked to a biomolecule.

4. The nanocomplex as claimed in claim 3, wherein the biomolecule is selected from the group consisting of a DNA, plasmid DNA, RNA, an antisense nucleotide, an aptamer, a protein, a glycoprotein, a polypeptide, a carbohydrate or a mixture of adduct of any two or more of these.

5. The nanocomplex as claimed in claim 1, wherein the nanocomplex has a maximal transfection efficiency of 7-9 orders in RLU/mg protein with minimal cytotoxicity.

6. The nanocomplex as claimed in claim 1, wherein the nanocomplex has a size in the range of 50 to 110 nm.

7. The nanocomplex as claimed in claim 1, wherein the nanocomplex carries biomolecules in the range of 20 bp to 7 kbp size.

8. A method of preparing the nanocomplex as claimed in claim 1, the method comprising:
   (a) providing Mgpe peptide selected from the group consisting of SEQ ID NOs: 3-6;
   (b) providing biomolecule selected from the group consisting of a DNA, plasmid DNA, RNA, an antisense nucleotide, an aptamer, a protein, a glycoprotein, a polypeptide, a carbohydrate or a mixture of adduct of any two or more of these;
   (c) diluting the peptide 10-100 µl obtained in step (a) and DNA 20-50 ng/µl obtained in step (b) in water such that peptide-DNA charge ratio is 0.5-50;
   (d) adding DNA solution obtained in step (b) drop-wise to an equal volume of the peptide dilution while vortexing; and
   (e) incubating solution obtained in step (d) for 30 min to 1 h at room temperature to obtain the nanocomplex.

9. A kit for delivering biomolecules into a cell, said kit comprising Mgpe peptide as claimed in claim 1 and an instruction manual, wherein the Mgpe peptide is selected from the group consisting of SEQ ID NOs: 3-6.

10. A method for delivery of nucleic acids into cells, comprising: providing a composition comprising the nanocomplex as claimed in claim 1, wherein the nanocomplex further comprises isolated nucleic acid selected for delivery to cells; and
   contacting cells with an amount of the composition effective to deliver the isolated nucleic acids into the cells.

11. A method for delivery of proteins to cells, comprising:
   providing a composition comprising the nanocomplex as claimed in claim 1, wherein the nanocomplex comprises isolated protein selected for delivery to cells; and
   contacting cells with an amount of the composition effective to deliver the isolated protein into the cells.

12. A method for delivery of biomolecules to cells, comprising:
   providing a composition comprising the nanocomplex as claimed in claim 1, wherein the nanocomplex comprises isolated biomolecules selected for delivery to cells; and
   contacting cells with an amount of the composition effective to deliver the isolated biomolecules to the cells.

13. The method of claim 12 wherein the cells are eukaryotic cells.

14. The method of claim 12 wherein the eukaryotic cells are cultured in a serum containing medium.

15. A composition, comprising: (a) nanocomplexes that comprise (i) an amphipathic peptide that comprises less than 30 amino acids and (b) at least one cell specific targeting ligand or immunogenic species or a drug associated with said nanocomplexes, wherein the amphipathic peptide comprises the amino acid sequence SEQ ID NO:3, SEQ ID NO:4, SEQ ID NO:5 or SEQ ID NO:6.

16. A method of forming the composition as claimed in claim 15, comprising synthesizing or modifying an immunogenic species or cell specific targeting ligand or a drug in the presence of nanocomplexes that comprise (i) an amphipathic peptide that comprises less than 30 amino acids, wherein the amphipathic peptide comprises the amino acid sequence SEQ ID NO:3, SEQ ID NO:4, SEQ ID NO:5 or SEQ ID NO:6, and wherein said synthesized or modified cell specific targeting ligand or immunogenic species or a drug is associated with said nanocomplexes as a result of said synthesis or modification step.

\* \* \* \* \*